United States Patent [19]

Schmidt

[11] Patent Number: 5,331,839
[45] Date of Patent: Jul. 26, 1994

[54] PROCESS FOR DETERMINING THE COEFFICIENT OF FRICTION M$\mu$

[75] Inventor: Günther Schmidt, Tamm, Fed. Rep. of Germany

[73] Assignee: Robert Bosch GmbH, Stuttgart, Fed. Rep. of Germany

[21] Appl. No.: 859,685

[22] PCT Filed: Jan. 19, 1991

[86] PCT No.: PCT/EP91/00099
§ 371 Date: Jun. 11, 1992
§ 102(e) Date: Jun. 11, 1992

[87] PCT Pub. No.: WO91/15386
PCT Pub. Date: Oct. 17, 1991

[30] Foreign Application Priority Data

Mar. 30, 1990 [DE] Fed. Rep. of Germany ....... 4010212

[51] Int. Cl.$^5$ ............................................ G01N 19/02
[52] U.S. Cl. ............................................ 73/9
[58] Field of Search ................. 73/9, 10; 364/426.01, 364/426.02, 426.03

[56] References Cited

U.S. PATENT DOCUMENTS

| 3,893,330 | 7/1975 | Shute et al. | 73/9 |
| 4,212,063 | 7/1980 | Härdmark | 364/426 |
| 4,779,447 | 10/1988 | Roth | 73/9 |

FOREIGN PATENT DOCUMENTS

| 2947259 | 5/1981 | Fed. Rep. of Germany. |
| 3516399 | 11/1986 | Fed. Rep. of Germany. |
| 3534022 | 3/1987 | Fed. Rep. of Germany. |
| 3705983 | 9/1987 | Fed. Rep. of Germany. |
| 3644139 | 7/1988 | Fed. Rep. of Germany. |
| 3828726 | 3/1989 | Fed. Rep. of Germany. |
| 3812824 | 11/1989 | Fed. Rep. of Germany. |

*Primary Examiner*—Hezron E. Williams
*Assistant Examiner*—Daniel S. Larkin
*Attorney, Agent, or Firm*—Spencer, Frank & Schneider

[57] ABSTRACT

A method for determining the coefficient of friction $\mu$ between the wheel and the road is described. Assuming a moving vehicle, the brake pressure on a non-driven wheel (measuring wheel) is increased until a tendency to lock occurs. At the same time, the driving torque is increased so that the braking force of the measuring wheel and the increased driving force of the driving wheel on the same vehicle side equal each other. Additionally, an increased driving force of the second driving wheel must be removed by braking.

18 Claims, 3 Drawing Sheets

PROCESS FOR DETERMINING THE COEFFICIENT OF FRICTION Mµ

BACKGROUND OF THE INVENTION

From DE-OS 37 05 983, a method is known for equipping a vehicle with an anti-locking brake system (ABS) and an automatic slip control (ASR). This reference, however, makes a method known by which only the coefficient of friction is determined and indicated in order to prompt the driver to adopt a mode of driving behavior which is adapted to the prevailing coefficient of friction. In the reference, the coefficient of friction is only determined during braking or acceleration of the vehicle.

SUMMARY OF THE INVENTION

In the present invention, determination of the current coefficient of friction between the tire and the road is desired at all times, not only during braking or acceleration, in order to be able to give early warning to the driver, for example at low friction values (snow, ice, wetness, etc.). In addition to the warning or in place of it, a visual or audible indication of the approximate coefficient of friction is possible.

If, in a front-wheel drive vehicle, for example, the right-hand front wheel VR is driven and the right-hand rear wheel HR is braked to the same degree, then there will be no change in the overall driving condition: the vehicle will continue to roll at the same speed V, but a tensioning condition will occur between front and rear wheels, and the lateral guiding forces will decrease on these wheels.

If the driving condition of the front wheel VR and the braking condition of the rear wheel HR are further increased (assuming that the output of the engine is sufficient), then the mutual tensioning condition will reach a value at which the front wheel VR will tend to spin and the rear wheel HR will tend to lock. This value $A_H$ has the following relation to the coefficient of road friction $\mu$:

$$A_H = \mu \times N_H/2$$

(assuming there are equal loading forces $N_H/2$ at the rear wheels).

If $N_H/2$ is known (by way of approximation, or to be on the safe side, an unladen vehicle is assumed), then the coefficient of friction can be calculated from the value $A_H$. The force $A_H$, in turn, is proportional to the braking force at the brake callipers or the pressure in the brake callipers. If this pressure is now created by being pulsed up from a constant pressure source via solenoid valves, then when taking into account the pressure-volume characteristic curve of the braking system, the sum of the accordingly corrected pulse times of the solenoid valve is a measure for the pressure in the brake callipers, and thus approximately proportional to the coefficient of road friction $\mu$. A pressure increase is also possible via a ramp function, e.g. through severely throttled solenoid valves in permanently open position. The word "continuously" is used to indicate that the pressure increase should not be sudden.

The invention is to be mainly applied where ABS-/ASR are used, since then only a few additional parts will be needed.

Since, with an increase in engine torque without braking, the second driven wheel would be accelerated and would create a yawing moment around the normal axis of the vehicle, it must be held at the speed prevailing when $\mu$ was first determined.

BRIEF DESCRIPTION OF THE DRAWINGS

Embodiments of the invention will be explained on the basis of the drawings.

The figures show the following.

DETAILED DESCRIPTION OF THE PREFERRED EMBODIMENTS

Figure 1:
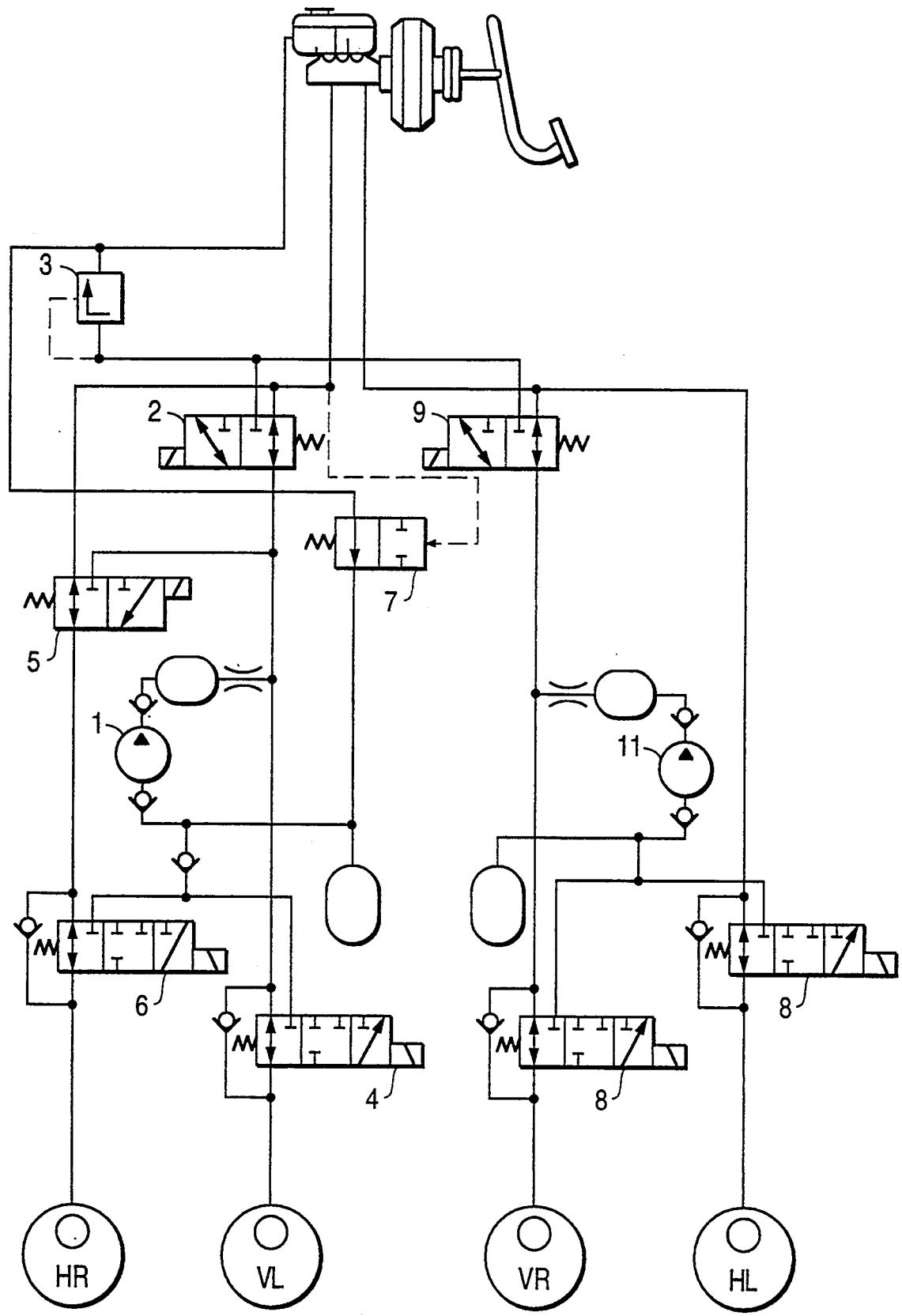
FIG. 1. A well-known ABS/ASR, which has been extended according to an embodiment of the invention.

FIG. 1 shows an ABS and ASR for a front-wheel drive vehicle with diagonal braking circuit splitting. In the case of the ASR, for the purpose of brake control, an ABS recirculating pump 1 is set in operation which creates the required brake pressure for the left front wheel VL. This pressure is then kept constant via a then switched changeover valve 2 and a pressure limiter 3. By means of a 3/3 ABS solenoid valve 4, the pressure at the brake of the left front wheel VL is then varied. The system also has a pressure-controlled loading valve 7 and a second ABS pump 1.

Similarly, in the case of the ASR, the pressure on the brake of the right front wheel VR is varied by valves 8 and 9.

For the purpose of the invention, an additional changeover valve 5 is now proposed.

If $\mu$ is to be determined at constant velocity, then a signal is produced, for example, by means of a key, which operates the changeover valves 2 and 5, and switches on pump 1. Via the ABS valves 4 and 6, pressure can now be induced individually to the brakes of the wheels HR and VL by a control device. Pressure is introduced in such a way that on the one hand the brake pressure on the rear right-hand wheel HR is progressively pulsed, while at the same time the drive output is increased so that the driving force of front right-hand the wheel VR and the braking force of the rear right-hand wheel HR approximately compensate each other, and on the other hand the braking force on the front right-hand wheel VL is increased in such a way that its speed is held approximately constant.

This control is continued until a tendency to lock occurs at the wheel HR. The number of pulses which were needed to reach this level of pressure represents a measure for the desired $\mu$ value on the right-hand side of the vehicle, where as a rule the more slippery track is found (where traffic travels on the right-hand side of the road).

The measuring action of $\mu$ can be triggered automatically if the vehicle is moving straight ahead at constant speed. If the driver brakes during measurement, then the measuring action is discontinued.

Figure 2:
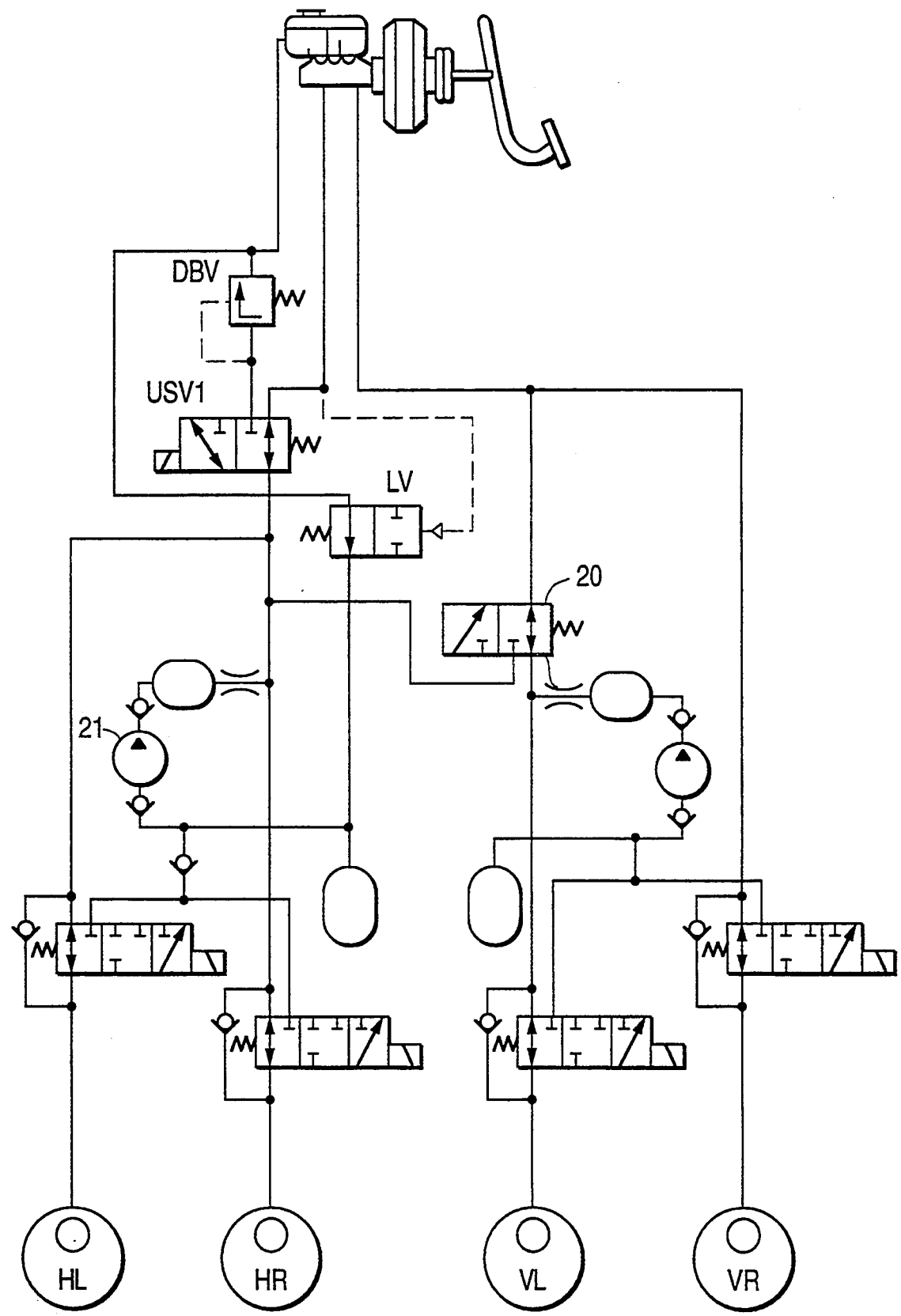
FIG. 2 A second ABS/ASR, which has also been extended according to a further embodiment of the invention.

In the embodiment of FIG. 2, a rear wheel drive vehicle with axis braking circuit splitting is assumed. Here, the right-hand front wheel VR is used as the measuring wheel for the measurement of $\mu$ and braked until the tendency to lock appears, the right-hand rear wheel HR is driven with increased output, and the left-hand rear wheel HL is braked to maintain constant revolutions. Additionally, with pump 21 switched on, a changeover valve 20 is also required in order to be able to supply the right-hand front wheel VR with brake pressure. In other respects, the parts in FIGS. 1 and 2 correspond to one another with parts DBN, USV1 and LV of FIG. 2 corresponding to parts 3, 2 and 7, respectively, of FIG. 1.

Figure 3:
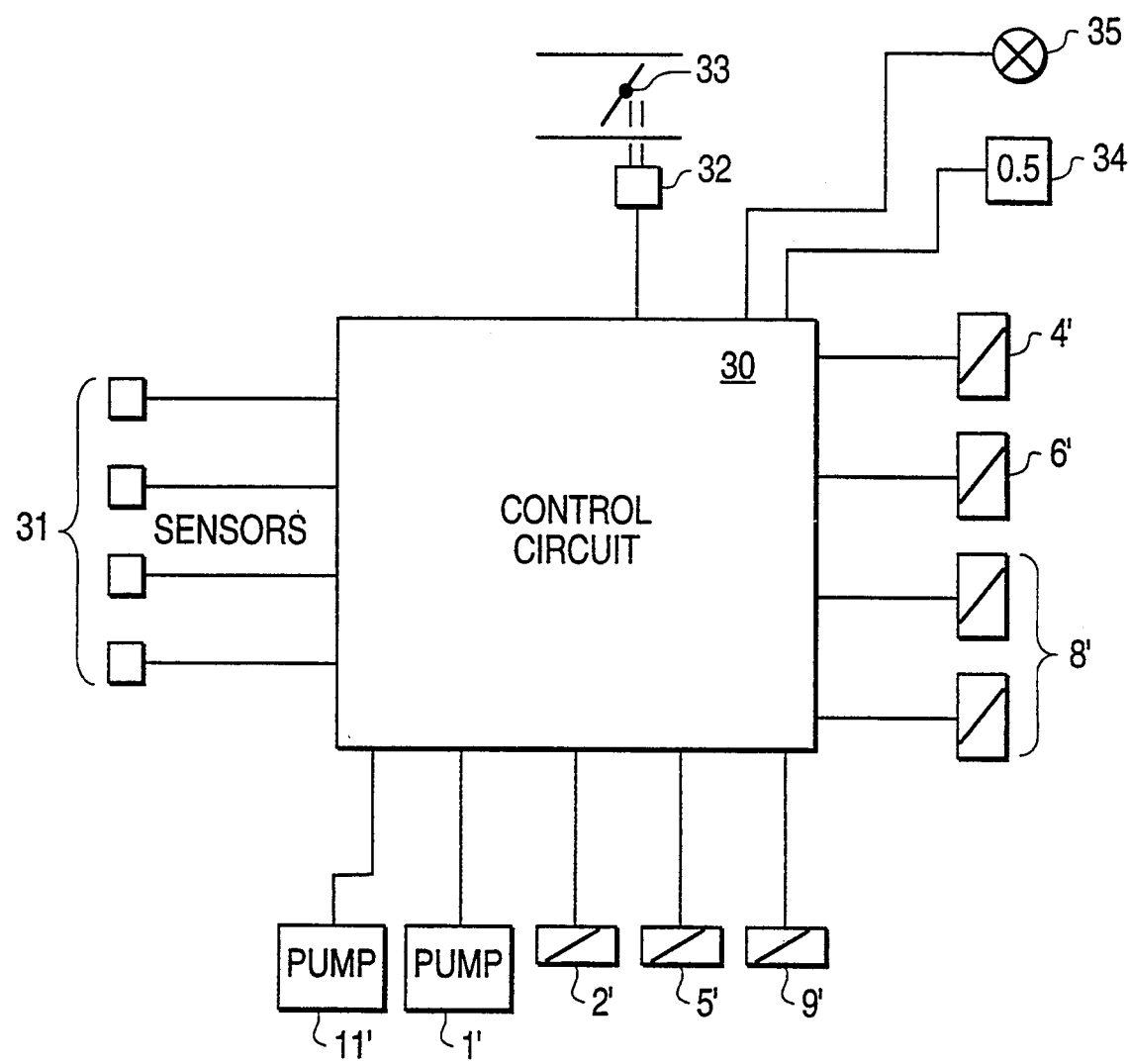
FIG. 3 An extended control circuit.

FIG. 3, shows the control circuit for the system of FIG. 1, this control circuit is designated 30. It is connected with four sensors 31 for registering the wheel speeds, with four ABS valves 4', 6' and 8' (corresponding to 4, 6 and 8 of FIG. 1), three changeover valves 2', 5' and 9', two pumps 1' and 11', and an actuator 32 for a throttle valve 33.

In the ABS case, two pumps 1' and 11' are in operation and the brake pressure is varied by means of the valves 4', 6' and 8', in accordance with the wheel movement behavior monitored via the sensors 31.

In the ASR case, the valves 2' and 9' are changed over and both pumps 1' and 11' are switched on. Pressure is varied on the front wheels by means of the valves 4' and 8'. In addition, the throttle valve 33 is adjusted, via the actuator 32 so as to reduce engine torque.

In the case of the measurement of $\mu$, the valves 2' and 5' are switched and both pumps 1' and 11' are running. By means of the valve 6, the brake pressure at the wheel HR is pulsed up. Simultaneously, controlled by the control device via the throttle valve actuator 32, the engine torque is increased so that the braking force of the wheel HR and the driving force of the wheel VR equal each other. The algorithm for controlling the driving force and the braking force must be designed specific to the vehicle. Programming takes place in the computer of the control device. Additionally, the wheel VL is now braked in such a way that despite increased driving force, its revolutions do not increase, but are maintained, for example, at the same revolutions of the wheel VL.

The number of pulses required to create the tendency to lock at the wheel VR is a measure of the desired coefficient of friction $\mu$, and this can then be indicated (display 34) after conversion, and/or trigger a warning (warning light 35).

I claim:

1. A method for determining a coefficient of friction $\mu$ between a tread of a tire of a vehicle, having at least two driven and at least two non-driven wheels, and a road surface, using pressure control devices for application of respective brake pressure at wheel brakes, and using control circuit, which receives signals corresponding to wheel speeds, for controlling the pressure control devices and for varying engine torque, wherein in the case where the vehicle is not being braked and is not significantly accelerated, the control circuit continuously increases, in response to a trigger signal at a start time, and by means of the pressure control devices, a brake pressure which produces a braking force on a measuring wheel which is not driven;

simultaneously, the control circuit increases engine output to increase a driving force on a first driven wheel on the same side of the vehicle as the measuring wheel such that the braking force of the measuring wheel and the driving force of the first driven wheel approximately compensate each other;

a second driven wheel is braked such that it remains approximately at a given speed; and a measuring time period required for increasing the brake pressure to produce locking of the measuring wheel is determined and used as a measure for the coefficient of friction.

2. A method in accordance with claim 1, wherein the braking pressure at the measuring wheel is produced by braking pulses, and the measuring time period is determined from the number of braking pulses.

3. A method in accordance with claim 1, wherein the given speed of the second driven wheel is approximately the same as a speed of a non-driven wheel on the same side of the vehicle.

4. A method in accordance with claim 2, wherein the increasing in the driving force on the first driven wheel takes place in steps.

5. A method in accordance with claim 1, wherein the coefficient of friction is indicated.

6. A method in accordance with claim 1, wherein when the coefficient of friction is below a threshold, at least one of an acoustic and a visual warning is given.

7. A method in accordance with claim 1, wherein the trigger signal is produced by a driver.

8. A method in accordance with claim 1, wherein the trigger signal is produced automatically.

9. A method in accordance with claim 1, wherein the given speed of the second driven wheel is approximately the same as a speed of the second driven wheel at the start time.

10. A method for determining a coefficient of friction ($\mu$) between a tread of a tire of a vehicle, having at least two driven and at least two non-driven wheels, and a road surface, in the case where the vehicle is not being braked and not significantly accelerated, using pressure control devices for application of brake pressure at respective wheel brakes, and using a control circuit, which receives signals corresponding to wheel speeds, for controlling the pressure control devices and for varying engine torque, the method comprising the steps of:

generating a trigger signal at a start time;

causing, in response to the trigger signal, a continuous increase in a brake pressure which produces a braking force on a measuring wheel which is a first non-driven wheel, and causing a simultaneous increase in the engine torque to increase a driving force on a first driven wheel on the same side of the vehicle as the measuring wheel such that the braking force of the measuring wheel and the driving force of the first driven wheel approximately compensate each other;

braking a second driven wheel such that it remains approximately at a given speed;

determining a measuring time period required for increasing the brake pressure to produce locking of the measuring wheel; and calculating the coefficient of friction based on the measuring time period.

11. A method in accordance with claim 10, wherein said step of causing includes producing the braking pressure at the measuring wheel by braking pulses, and wherein said step of determining includes determining the measuring time period from the number of braking pulses.

12. A method in accordance with claim 11, wherein said step of causing includes increasing the driving force on the first driven wheel in steps.

13. A method in accordance with claim 10, wherein said step of braking includes causing the given speed of the second driven wheel to be approximately the same as a speed of a second non-driven wheel on the same side of the vehicle.

14. A method in accordance with claim 10, further comprising a step of indicating the coefficient of friction.

15. A method in accordance with claim 10, further comprising a step of determining whether the coefficient of friction is below a threshold, and a step of providing at least one of an acoustic and visual warning if the coefficient of friction is below the threshold.

16. A method in accordance with claim 10, wherein said step of generating includes a vehicle driver producing the trigger signal.

17. A method in accordance with claim 10, wherein said step of generating includes producing the trigger signal automatically.

18. A method in accordance with claim 10, wherein said step of braking includes causing the given speed of the second driven wheel to be approximately the same as a speed of the second driven wheel at the start time.

* * * * *